US00PP25164P3

(12) United States Plant Patent
Bors

(10) Patent No.: US PP25,164 P3
(45) Date of Patent: Dec. 9, 2014

(54) COLEUS PLANT NAMED 'H67'

(50) Latin Name: *Solenostemon* sp.
Varietal Denomination: H67

(75) Inventor: Robert H. Bors, Saskatoon (CA)

(73) Assignee: University of Saskatchewan Department of Plant Sciences, Saskatoon, Saskatchewan (CA)

( * ) Notice: Subject to any disclaimer, the term of this patent is extended or adjusted under 35 U.S.C. 154(b) by 247 days.

(21) Appl. No.: 13/506,718

(22) Filed: May 10, 2012

(65) Prior Publication Data

US 2013/0305419 P1 Nov. 14, 2013

(51) Int. Cl.
*A01H 5/00* (2006.01)

(52) U.S. Cl.
USPC ..... Plt./373; Plt./263.1

(58) Field of Classification Search
USPC ..... Plt./373, 263.1
See application file for complete search history.

*Primary Examiner* — Susan McCormick Ewoldt
*Assistant Examiner* — Louanne Krawczewicz Myer
(74) *Attorney, Agent, or Firm* — Barbara Campbell; Cochran Freund & Young LLC

(57) ABSTRACT

A Coleus plant particularly distinguished by triangular leaves with many deep lobes and yellow-green leaves with purple margins, is disclosed.

2 Drawing Sheets

Genus and species: *Solenostemon* sp.
Variety denomination: 'H67'.

BACKGROUND OF THE NEW PLANT

The present invention comprises a new and distinct variety of Coleus, botanically known as *Solenostemon* sp., and hereinafter referred to by the variety name 'H67'. The new variety originated from an open pollination conducted in Saskatoon, Saskatchewan, Canada in the winter 2007-2008. 'H67' is the result of 4 generations of open pollination descending from 'Coleus#3' (unpatented) with 'Coleus#21' (unpatented). The seeds produced by the open pollination were sown in April 2008. A single plant selection was chosen for further evaluation and asexual propagation in December 2008.

The new plant was first asexually propagated in December 2008 in Saskatoon, Saskatchewan, Canada and has been asexually reproduced by vegetative cuttings for almost three years in Saskatoon, Saskatchewan, Canada. The present invention has been found to retain its distinctive characteristics through successive asexual propagations by vegetative cuttings.

'H67' has not been made publicly available or sold more than one year prior to the filing date of this application.

SUMMARY OF THE NEW PLANT

The following are the most outstanding and distinguishing characteristics of the new variety when grown under normal horticultural practices in Saskatoon, Saskatchewan, Canada and Litchfield, Mich.

1. Triangular shaped leaves with many deep lobes;
2. Leaves larger than 'Kiwi Fern' but smaller than most coleus;
3. Yellow-green leaves with purple margins and;
4. Under sunny conditions more purple appears in the center of the leaves.

DESCRIPTION OF THE PHOTOGRAPHS

This new Coleus plant is illustrated by the accompanying photographs which show the overall plant habit, and foliage of the plant. The colors are as true as can be reasonably obtained by conventional photographic procedures. The photographs are of a 4.5 month-old plant grown in a greenhouse in Litchfield, Mich. The photographs were taken in November 2011.

Figure 1:
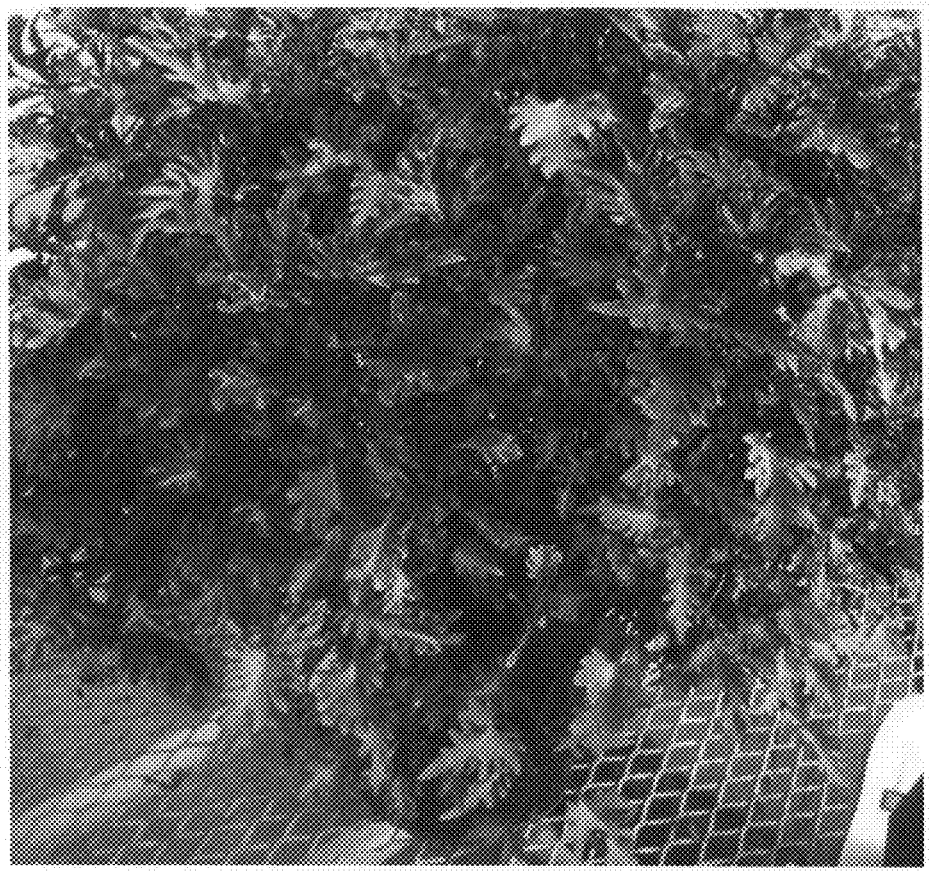
Figure 2:
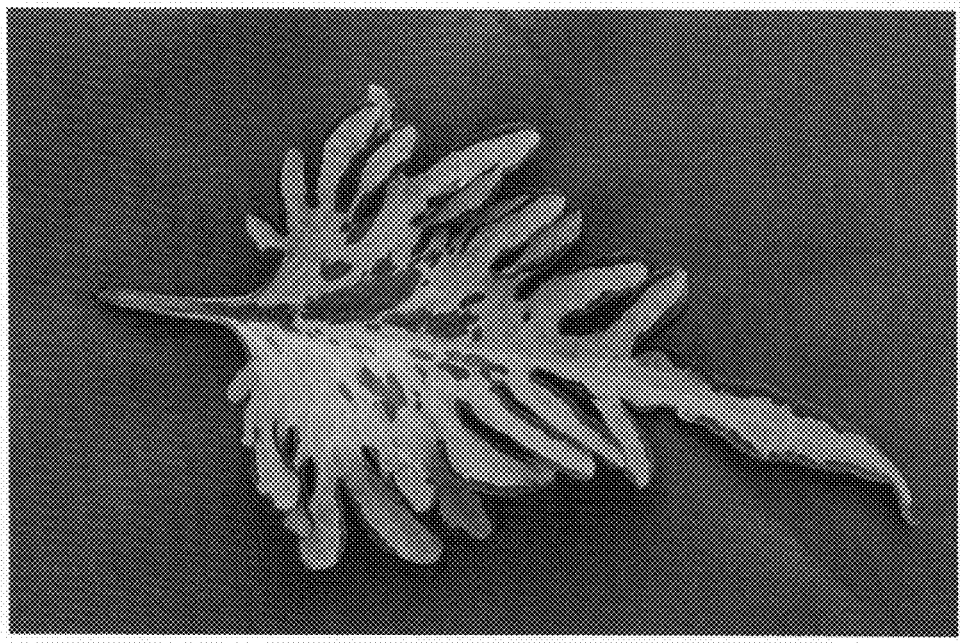

FIG. 1 shows the whole plant, including habit and foliage.
FIG. 2 shows a close-up of the foliage.

DESCRIPTION OF THE NEW VARIETY

The following detailed descriptions set forth the distinctive characteristics of 'H67'. The data which defines these characteristics were collected from asexual reproductions carried out in Saskatoon, Saskatchewan, Canada. The plant history was taken in October 2011 on 16-week old plants grown in a greenhouse in Litchfield, Mich. Color references were taken under natural light and are to The R.H.S. Colour Chart of The Royal Horticultural Society of London (R.H.S.), fifth edition (2007).

Classification:
*Family*.—Lamiaceae.
*Botanical name*.—*Solenostemon* sp.
*Common name*.—Coleus.
*Denomination*.—'H67'.

Parentage: 'H67' is the result of 4 generations of open pollination descending from 'Coleus#3' (unpatented) with 'Coleus#21' (unpatented).

Plant:
*Type*.—Annual.
*Habit*.—Upright, basal-branched.
*Height* (*measured from the top of the soil*).—40.6 cm.
*Width* (*horizontal plant diameter*).—55.9 cm.
*Time to produce a finished plant*.—About 6 to 8 weeks.
*Time to initiate and develop roots*.—About 3 weeks.
*Root description and habit*.—White roots, fibrous, and branching.
*Propagation type*.—Vegetative cuttings.

Branches:

*Quantity per plant.*—6 primary branches; multiple secondary branches.

*Length.*—35.6 cm.

*Internode length.*—1.3 cm to 3.8 cm.

*Diameter (from midpoint).*—0.6 cm.

*Color.*—RHS N77A (Purple).

*Texture.*—Smooth.

*Petiole.*—Color: RHS N77A (Purple). Length: 3.8 cm. Diameter: 0.2 cm. Texture: Smooth.

Leaves:

*Quantity of leaves per branch.*—About 16 to 20.

*Arrangement.*—Opposite/Sub-opposite.

*Length.*—5.1 cm to 6.4 cm.

*Width.*—2.5 cm to 4.4 cm.

*Appearance.*—Deeply lobed with 8 to 20 lobes per leaf.

*Shape.*—General shape is triangular with the base being half as long as the length; length of lobes is about one-third of the length of the leaves; the apex of the leaves is a single lobe and the lobes are about one-third of an inch wide; the margin color is about about one-tenth of an inch wide.

*Base.*—Truncate.

*Margin.*—Deeply clefted, with lobes on either side being larger than the mid-section.

*Fragrance.*—Absent.

*Color, immature.*—Upper surface: RHS 146B (Yellow-green) and RHS N77A (Purple) on the margins. Lower surface: RHS N77A (Purple).

*Color, mature.*—Upper surface: RHS 146B (Yellow-green) and RHS N77A (Purple) on the margins. Lower surface: RHS N77A (Purple).

*Texture.*—Upper surface: Smooth. Lower surface: Smooth.

*Venation type.*—Venulate. Venation color: Upper surface: RHS 146D (Yellow-green). Lower surface: RHS 146D (Yellow-green).

Inflorescence: Single, bilabiate flowers arranged in verticallasters on terminal spikes; 5 petals.

*Fragrance.*—Absent.

*Flowering season.*—Flowering is light and can occur under long days at any month of the year; flowering can occur under short days of winter if additional light is provided in the greenhouse.

*Lastingness of flowers on the plant.*—Individual flowers last one week, but the flower trusses (inflorescence) last 8 weeks.

*Spike.*—Length: 12.0 cm to 15.0 cm. Diameter: 2.5 cm to 3.0 cm. Quantity of verticillasters per spike: 7 flowers per node (18 to 42 nodes). Quantity per open flowers per verticillasters: Varies with age of plant.

*Flower bud.*—Length: 0.1 cm to 0.3 cm. Diameter: 0.1 cm to 0.2 cm. Color at tight bud: RHS 101B (Blue) with RHS 155B (White).

*Corolla.*—Diameter: 0.3 cm to 0.4 cm. Length: 1.0 cm to 1.1 cm. Petal arrangement: All 5 petals fused to form a tube. Banner petal width: 0.3 cm. Banner petal length: 0.4 cm. Banner petal apex: Obcordate with deep division. Banner petal margin: Entire. Banner petal color: Upper and lower surfaces are mostly RHS 155B (White) with the upper edge sometimes having a small spot of RHS 101B. Keel petal length: 0.7 cm to 0.8 cm. Keel petal width: 0.2 cm to 0.3 cm. Keel petal color (both upper and lower surfaces): RHS 101B (Blue). Keel petal apex: Rounded. Keel petal margin: Entire.

*Calyx.*—Form: One single calyx tube formed by 5 fused sepals. Calyx apex: Acuminate. Sepal description: Sepals are triangular in shape coming to a curved point. Length: 0.7 cm to 1.5 cm. Diameter: 0.2 cm. Color (both inner and outer surfaces): Variable mixture of RHS 150 (Yellow-Green), RHS 149 (Yellow-Green) and RHS 72A (Red-Purple). Calyxes are mostly the Yellow-Green colors but the Red-Purple can appear at the apex or base. Texture (both inner and outer surfaces): Slightly pubescent.

*Pedicels.*—Length: 0.4 cm. Width (diameter): Less than 0.1 cm. Texture: Hirsute. Color: RHS 71A (Dark Red-purple).

Reproductive organs:

*Stamens.*—Quantity per flower: 4. Filament color: White. Filament length: 0.8 cm to 0.9 cm. Anther shape: Oval. Anther length: Less than 0.1 cm. Pollen color: White. Pollen amount: Sparse.

*Pistils.*—Quantity per flower: 1. Length: 1.0 cm to 1.1 cm. Stigma color: Lavender. Stigma shape: Forked end. Style color: White. Ovary color: Black.

Disease or insect resistance: No disease or insect resistance observed.

COMPARISON WITH PARENTAL LINES AND COMMERCIAL VARIETY

'H67' differs from the commercial comparison 'Kiwi Fern' (patent status unknown) in that 'H67' has yellow-green leaves with purple margins, while 'Kiwi Fern' has brown leaves. Additionally, 'H67' has larger leaves and is less branching than 'Kiwi Fern'. 'H67' leaves have a triangular shape while 'Kiwi Fern' is more cylindrical

COMPARISON WITH PARENTAL LINES

'H67' differs from the parental varieties as shown in Table 1.

TABLE 1

| Characteristic | 'H67' | 'Coleus#3' | 'Coleus#21' |
|---|---|---|---|
| Leaf description | Yellow-green leaves with purple margins; deeply lobed | Larger leaves than 'H67'; no lobes | Leaves have a white mid-vein, pink interior and green margins |
| Plant size | Smaller plant size than 'Coleus#3' | Larger plant than 'H67' | |

I claim:

1. A new and distinct variety of Coleus plant as shown and described herein.

* * * * *